US012590111B2

(12) United States Patent
Yorgan et al.

(10) Patent No.: US 12,590,111 B2
(45) Date of Patent: Mar. 31, 2026

(54) FLAVONOID DERIVATIVE FOR TREATING DENTAL CARIES

(71) Applicant: Mühlbauer Technology GmbH, Hamburg (DE)

(72) Inventors: Kaja Yorgan, Halstenbek (DE); Olav-Sven Becker, Scheggerott (DE)

(73) Assignee: Mühlbauer Technology GmbH, Hamburg (DE)

( * ) Notice: Subject to any disclaimer, the term of this patent is extended or adjusted under 35 U.S.C. 154(b) by 1033 days.

(21) Appl. No.: 17/637,029

(22) PCT Filed: Aug. 20, 2020

(86) PCT No.: PCT/EP2020/073348

§ 371 (c)(1),
(2) Date: Feb. 21, 2022

(87) PCT Pub. No.: WO2021/032844

PCT Pub. Date: Feb. 25, 2021

(65) Prior Publication Data

US 2022/0281903 A1 Sep. 8, 2022

(30) Foreign Application Priority Data

Aug. 22, 2019 (DE) ..................... 10 2019 122 569.8

(51) Int. Cl.

| | |
|---|---|
| ***C07F 9/655*** | (2006.01) |
| ***A61K 8/55*** | (2006.01) |
| ***A61K 9/68*** | (2006.01) |
| ***A61K 47/54*** | (2017.01) |
| ***A61Q 11/00*** | (2006.01) |

(52) U.S. Cl.

CPC ............ *C07F 9/65522* (2013.01); *A61K 8/55* (2013.01); *A61K 9/0058* (2013.01); *A61K 47/548* (2017.08); *A61Q 11/00* (2013.01)

(58) Field of Classification Search

CPC ..... C07F 9/65522; A61K 47/548; A61K 8/55; A61K 9/0058; A61Q 11/00

USPC ........................................................ 514/100

See application file for complete search history.

(56) References Cited

U.S. PATENT DOCUMENTS

| | | | |
|---|---|---|---|
| 4,661,641 | A | 4/1987 | Lukac et al. |
| 4,883,887 | A | 11/1989 | Bernhard et al. |
| 2010/0226943 | A1 | 9/2010 | Brennan et al. |
| 2014/0314686 | A1 | 10/2014 | Birbara et al. |
| 2015/0374634 | A1 | 12/2015 | Koo et al. |

FOREIGN PATENT DOCUMENTS

| | | | |
|---|---|---|---|
| CA | 2004304 | A1 | 6/1990 |
| CN | 101613334 | | 12/2009 |
| CN | 102516301 | | 6/2012 |
| CN | 106187970 | | 12/2016 |
| EP | 1645272 | | 4/2006 |
| EP | 2902399 | | 8/2015 |
| WO | WO 2008/054475 | | 5/2008 |
| WO | WO 2010/019511 | | 2/2010 |

OTHER PUBLICATIONS

Written Opinion for PCT/EP2020/073348. Mailed Oct. 28, 2020. 16 pages.

International Search Report for PCT/EP2020/073348. Mailed Oct. 28, 2020. 18 pages.

*Primary Examiner* — Kristin A Vajda

(74) *Attorney, Agent, or Firm* — Casimir Jones, S.C.; Anne M. Reynolds

(57) ABSTRACT

The invention relates to a flavonoid derivative containing a flavonoid that is coupled to an alkylene group via an ether bond, said alkylene group having an adhesion group for adhesion onto a dental surface. The flavonoid derivative has a long-term suppressing effect on the dental disease-causing formation of biofilm on the dental surfaces treated with the flavonoid derivative. The invention further relates to a kit for producing such a flavonoid derivative, and to the use of same.

(Formel V)

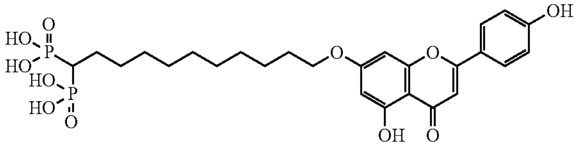

AA Glucosyltransferase
BB Sucrose
CC Glucan
DD Fructose

15 Claims, 4 Drawing Sheets

Sucrose

Glucan

Fructose

FLAVONOID DERIVATIVE FOR TREATING DENTAL CARIES

FIELD OF THE INVENTION

The invention relates to a flavonoid derivative. The invention also relates to the use of this flavonoid derivative in dentistry, in particular in dental prophylaxis and the treatment of dental caries, and a process for production thereof.

BACKGROUND

The use of flavonoids to inhibit glucosyl transferases of biofilm-forming streptococci that cause caries, is known from US 2015/374634 A1. The flavonoid is located inside a nanoparticle that dissolves in the acidic pH range and is released in the acidic environment of a biofilm, as shown schematically in FIG. 5 of US 2015/374634 A1. As can also be seen from FIG. 5 of US 2015/374634 A1, the invention aims at a short-term treatment of an already existing biofilm or a pellicle layer on a tooth surface, while binding of the flavonoid to the tooth surface for longer-term provision on the same for anti-streptococcal prophylaxis or control of the biofilm-forming streptococci is not provided. In addition, a permanent and stable bonding of the flavonoid to a surface, in particular a tooth surface, would also not be possible with the materials proposed in US 2015/374634 A1 for the nanoparticle shell, since the flavonoid is bound to the shell material via readily hydrolyzable groups . The use of said readily hydrolyzable groups is also within the meaning of the invention of US 2015/374634 A1, since the flavonoid active ingredient should be cleaved off rapidly under the acidic conditions of a biofilm in order to be available for a short time against the caries-causing streptococci in the biofilm.

The reasons for the formation of biofilm and influence thereof on dental caries is known from the prior art and is briefly summarized below:

*Streptococcus mutans* (*S. mutans*) is considered to be the most important cause of caries. In addition to lactic acid production and acid tolerance, the production of extracellular glucans is one of the most important virulence factors of this pathogen. Glucans are synthesized from sucrose by glucosyltransferases (Gtfs), as shown in FIG. 1 (illustration of glucan synthesis by glucosyltransferases) of the present application. These glucans contribute to the development and establishment of cariogenic biofilms by promoting adherence and accumulation of cariogenic streptococci on the tooth surface and making a decisive contribution to the structural integrity of plaque. *S. mutans* produces at least three Gtfs: Gtf B, which synthesizes insoluble glucan (α1, 3-linked); Gtf C, which produces a mixture of insoluble and soluble glucan (a 1,6-linked); and Gtf D, which synthesizes soluble glucan. Enzymatically active Gtfs are present (i) throughout human saliva, (ii) in the pellicle layer and (iii) on bacterial surfaces. Therapeutic approaches to preventing glucan production by inhibiting Gtfs are therefore an effective approach.

The approach selected in US 2015/374634 A1 and outlined at the beginning, based on the cleavage of the flavonoid from its binding partner under oral conditions, in particular under the acidic conditions in or near the biofilm, has a number of disadvantages. One disadvantage is the limited quantitative availability of the flavonoid, which is predetermined by the maximum possible loading of the nanoparticle core. The amount of flavonoid active ingredient that can be released and thus available on the biofilm near the tooth surface is thus severely limited, so that the flavonoid active ingredient may not be sufficient for a sustained effect, especially if a strong biofilm has already formed. A further disadvantage is the only short-term availability of the flavonoid at the site of action, since the flavonoid active ingredient lacks a stable bond to the tooth surface, in particular one that is stable to hydrolysis under oral conditions. When the nanoparticles dissolve under acidic pH conditions in the oral cavity, especially when acid-containing food is ingested, the flavonoid active ingredient is released and is swallowed into the oesophagus after a short time due to the lack of stable adhesion to the tooth surface and hydrolytic cleavage from the nanoparticle shell material. This occurs even in the best case. In the less favourable case, the nanoparticles containing the flavonoid active ingredient are even swallowed directly after being introduced into the oral cavity, i.e. even before the flavonoid active ingredient is released from the nanoparticle shell and could be cleaved therefrom. Even if the nanoparticle has found its way into the biofilm and is embedded therein, it can hardly develop its therapeutic effect if the biofilm leaves the oral cavity prematurely and without prior release of the flavonoid as a result of (e.g. mechanical) abrasion during food intake or tooth brushing.

SUMMARY OF THE INVENTION

The object of the invention is to avoid the aforementioned disadvantages and also to create a flavonoid derivative suitable for prophylactic use in addition to improvements in the treatment of dental caries.

To achieve this object, the invention proposes a flavonoid derivative according to claim 1, in which the flavonoid may be bonded to a tooth surface, via an ether bond and spacer group that is stable to hydrolysis under oral conditions, by means of a specific adhesion group, i.e. a flavonoid derivative A-Et-Q-Z comprising i) a spacer group Q, coupled to a flavonoid A via an ether bond Et, wherein the spacer group Q is an alkylene group, which may optionally be interrupted by an oxygen atom, a nitrogen atom and/or a polyoxyalkylene group, and ii) at least one adhesion group Z coupled to the spacer group Q, said Z group being selected from the group consisting of:

$—COOR^2$, $—SO_2OR^2$, $—OPO(OR^2)_2$, $—PO(OR^2)_2$, $—CR^1(PO(OR^2)_2)_2$, preferably $—PO(OR^2)_2$, $—CR^1(PO(OR^2)_2)_2$, where $R^1$=H, OH or alkyl, $R^2$=H, alkyl or M, where M is a monovalent cation, preferably a monovalent metal cation, in particular a sodium ion;

particularly preferably $—CH(PO(OH)_2)_2$.

Said flavonoid derivative comprises a flavonoid A, which inhibits at least one glucosyltransferase from streptococcal lactic acid bacteria, as shown in the working examples of the present application. Said streptococci are preferably selected from the *Streptococcus mutans* group and the *Streptococcus downei* group, in particular *Streptococcus mutans* and *Streptococcus sobrinus,* preferably *Streptococcus mutans.*

If the adhesion group Z, coupled to the spacer group Q, is $—COOR^2$, then said spacer Q preferably comprises a linear alkylene group having 8 to 12 carbon atoms.

The flavonoid derivative according to the invention may be selected from the formulae I-V shown below:

(Formula I)

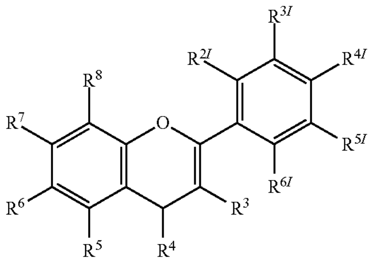

where i) $R^4$=H, OH or an oxo group (=O);

ii) $R^3$, $R^5$, $R^6$, $R^7$, $R^8$, $R^{2I}$, $R^{3I}$, $R^{4I}$, $R^{5I}$, $R^{6I}$ are each independently H, OH, $OR^1$ where $R^1$=methyl or acyl, rhamnose, glucose, oligoglucose, rutinose or Et-Q-Z where Et=O, i.e. O-Q-Z, and iii) at least one of the radicals $R^3$, $R^5$, $R^6$, $R^7$, $R^8$, $R^{2I}$, $R^{3I}$, $R^{4I}$, $R^{5I}$, $R^{6I}$, preferably $R^6$, $R^7$, $R^8$ $R^{3I}$, $R^{4I}$ or $R^{5I}$, particularly preferably $R^7$ or $R^{4I}$, is Et-Q-Z where Et=O, i.e. O-Q-Z;

(Formula II)

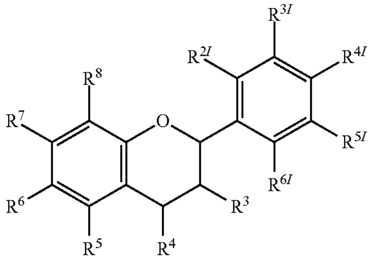

(Formula III)

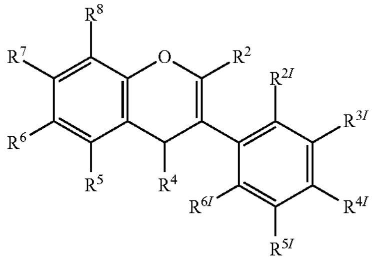

where i) $R^4$=H, OH or an oxo group (=O);

ii) $R^2$, $R^5$, $R^6$, $R^7$, $R^8$, $R^{2I}$, $R^{3I}$, $R^{4I}$, $R^{5I}$, $R^{6I}$ are each independently H, OH, $OR^1$ where $R^1$=methyl or acyl, rhamnose, glucose, oligoglucose, rutinose or Et-Q-Z where Et=O, i.e. O-Q-Z, and iii) at least one of the radicals $R^2$, $R^5$, $R^6$, $R^7$, $R^8$, $R^{2I}$, $R^{3I}$, $R^{4I}$, $R^{5I}$, $R^{6I}$, preferably $R^6$, $R^7$, $R^8$ $R^{3I}$, $R^{4I}$ or $R^{5I}$, particularly preferably $R^7$ or $R^{4I}$, is Et-Q-Z where Et=O, i.e. O-Q-Z and wherein said flavonoid derivative is preferably a flavonoid derivative according to formula (Formula IV)

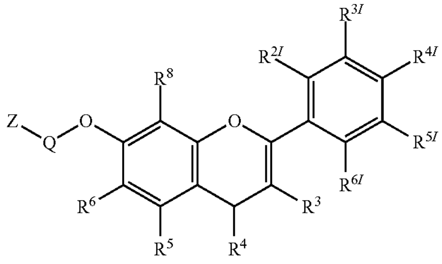

and more preferably according to formula (Formula V)

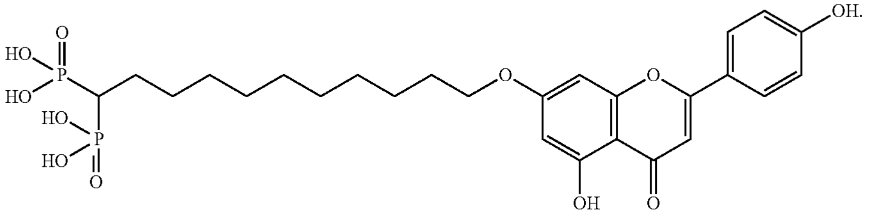

where i) $R^4$=H, OH or an oxo group (=O);

ii) $R^3$, $R^5$, $R^6$, $R^7$, $R^8$, $R^{2I}$, $R^{3I}$, $R^{4I}$, $R^{5I}$, $R^{6I}$ are each independently H, OH, $OR^1$ where $R^1$=methyl or acyl, rhamnose, glucose, oligoglucose, rutinose or Et-Q-Z where Et=O, i.e. O-Q-Z, and iii) at least one of the radicals $R^3$, $R^5$, $R^6$, $R^7$, $R^8$, $R^{2I}$, $R^{3I}$, $R^{4I}$, $R^{5I}$, $R^{6I}$, preferably $R^6$, $R^7$, $R^8$ $R^{3I}$, $R^{4I}$ or $R^{5I}$, particularly preferably $R^7$ or $R^{4I}$, is Et-Q-Z where Et=O, i.e. O-Q-Z In the flavonoid derivative according to the invention, the flavonoid A is preferably derived from the group of flavones, isoflavones, flavonols, flavanols, flavanones and flavanonols, preferably comprising at least one hydroxyl group on the benzyl and/or phenyl ring. For instance, the flavonoid A may be selected from apigenin, acacetin, baicalein, chrysin, luteolin, kaempferol, kaempferide, galangin, isorhamnetin, rhamnetin, myricetin, fisetin, pinobanksin, pinobanksin 3-acetate, pinocembrin, sakuranetin, isosakuranetin, quercetin, hesperetin, naringenin, trihydroxymethoxyflavanones, tetrahydroxyflavanones, ermanin, 7-hydroxyflavone, 7,8-dihydroxyflavone, daidzein, genistein, gengwanin, quercitrin, epicatechin, epicatechin gallate, epigallocatechin, epigallocatechin gallate, 3,5,7-trihydroxy-4'-methoxyflavanol, 5,6,7-trihydroxy-3,4'-dimethoxyflavone, 3,7-dihydroxy-5-methoxyflavanone, 2,5-dihydroxy-7-methoxyflavanone, 8-methylkaempferol. Particularly preferred are apigenin, kaempferol, chrysin, daidzein, quercetin and epigallocatechin gallate, and most preferred is apigenin.

In the flavonoid derivative according to the invention, the adhesion group Z is preferably covalently bonded to the spacer group Q via a C—C bond, a C—S bond, a C—P bond, a C—O—P bond or a C—C—P bond.

Said spacer Q is preferably a linear or branched alkylene having alicyclic units, and comprises, for example, 3 to 20, preferably 5 to 18, more preferably 7 to 16 carbon atoms, particularly preferably a linear alkylene group having 8 to 12 carbon atoms, preferably a decanylene group, or the spacer Q is a polyether group having 2 to 10 alkoxy units, preferably selected from ethylene glycol units [$—O—CH_2—CH_2—$] and propylene glycol units [$—O—CH_2—CH(CH_3)—$], preferably a polyether group having 4 ethylene glycol or propylene glycol units.

The flavonoid derivative A-Et-Q-Z according to the invention can be produced in a process comprising the following steps:

a) ether synthesis of
   i) a flavonoid A, wherein said flavonoid A is selected from the group consisting of flavones, isoflavones, flavonols, flavanols, flavanones and flavanonols, and comprises at least one hydroxyl group (—OH) on the benzyl and/or on the phenyl ring,
   with
   ii) a compound comprising firstly a bromine atom (Br) covalently bonded to the spacer group Q and secondly a group XZ covalently bonded to the spacer group Q, wherein said group XZ is preferably an acid ester group, which in a further process step may be converted to the adhesion group Z,
   as shown below: XZ-Q-Br+HO-A→XZ-Q-O-A;
b) conversion of the group XZ bonded to the spacer group Q, preferably by hydrolysis, to the adhesion group Z and obtaining the flavonoid derivative A-Et-Q-Z as shown below, where Et=O: XZ-Q-O-A→Z-Q-O-A.

A flavonoid derivative produced by this process is also an object of the invention defined in the claims.

The flavonoid derivative according to the invention or two or more of the flavonoid derivatives according to the invention different from one another may be constituents of a carrier and/or a dental preparation, wherein said carrier and/or dental preparation is preferably selected from the group consisting of: paste, gel, coating, foam or else mouthwash, chewing gum and chewable tablet.

In a preferred embodiment of the invention, the flavonoid derivative or the carrier and/or the dental preparation comprises at least one further active ingredient, preferably selected from the group of the flavonoids, in particular the catechins.

The carrier and/or the dental preparation may comprise a fluoridating agent, preferably selected from the group of metal fluorides, amine fluorides and fluoride complexes, in particular sodium fluoride.

The flavonoid derivative according to the invention or the carrier and/or the dental preparation are suitable for use as a medicament, in particular for the prophylaxis and/or treatment of an oral disease, preferably for the prophylaxis and/or treatment of dental caries.

The flavonoid derivative or the carrier and/or the dental preparation are suitable for preventing the formation of a new biofilm and/or accumulation of a biofilm. In addition, they are suitable for treating a biofilm, preferably a biofilm formed by *Streptococcus mutans*, wherein said biofilm is more preferably in the oral cavity of a patient on the tooth surface.

The present invention, as defined in the claims, further relates to a method, preferably in vitro method, for preventing the formation of a new biofilm and/or accumulation of a biofilm and/or for treating a biofilm, preferably a biofilm formed by *Streptococcus mutans*, on a surface comprising hydroxyapatite, such as a tooth surface for example. The method comprises the following steps: a) providing i) a flavonoid derivative described above or a carrier and/or a dental preparation and ii) a surface comprising hydroxyapatite with a biofilm optionally present on the surface; and b) treating ii) with i).

Said method is preferably carried out during professional tooth cleaning (PTC) or immediately after professional tooth cleaning. For instance, after cleaning the tooth surfaces with the flavonoid derivative according to the invention, they may be treated in a mouthwash by rinsing the oral cavity for 10 seconds. Said method may furthermore optionally comprise repeating step b) at an interval of at least 1 week, preferably at least 1 month, more preferably at least 3 months and no longer than 24 months, preferably no longer than 12 months, particularly preferably after 6 months.

DETAILED DESCRIPTION

Figure 3:
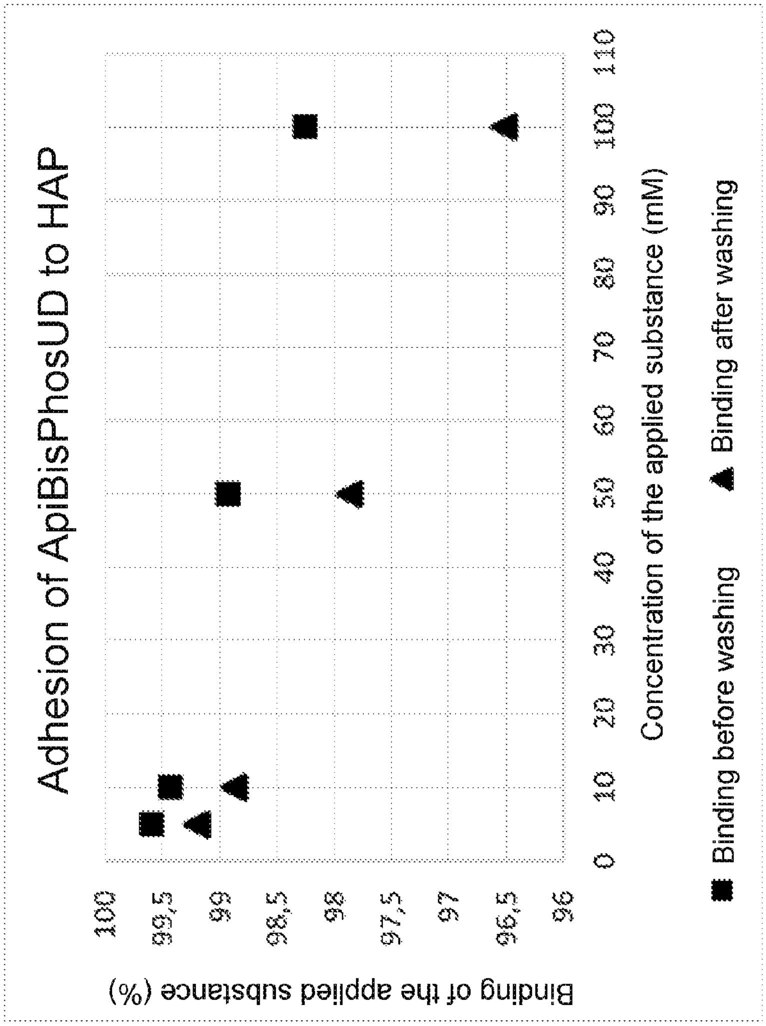
FIG. 3 shows data demonstrating that the flavord derivative "ApiBisPhos UD" according to the invention adheres excellently to the hydroxyapatite moistened with saliva with more than 96% of the applied ApiBsPhos UD substrate binding.
Figure 4:
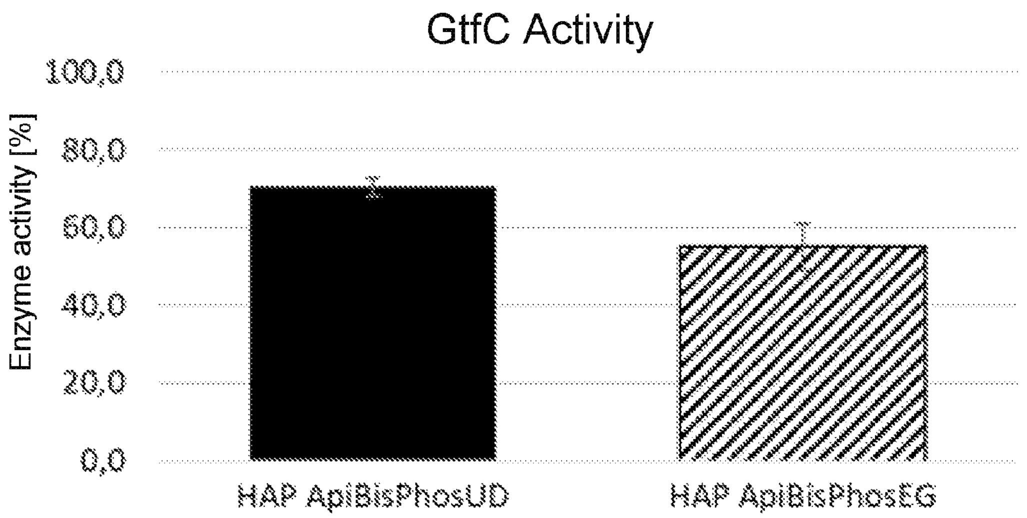
FIG. 4 shows data demonstrating that both ApiBisPhos UD and ApiBisPhos EG bound to hydroxyapatite inhibit the GtfC enzyme activity of *S. mutans* to a considerable degree.

The present invention is described in more detail with the aid of Examples 1-6 below and FIGS. 2-4.

The following chemicals were used in Examples 1 and 2:

acetone (dried over molecular sieves),
apigenin (Apollo Scientific Ltd.),
1,10-dibromodecane,
dimethyl sulfoxide (dried over molecular sieves),
ethanol,
ethyl acetate,
n-heptane,
potassium hydroxide,
lithium bromide, anhydrous (ChemPUR GmbH),
tetraisopropylmethylene bisphosphonate (TCI Deutschland GmbH),
sodium hydride,
sodium hydrogen carbonate,
tetraethylene glycol di-p-toluenesulfonate (TCI Deutschland GmbH)

tetrahydrofuran, anhydrous,
toluene,
hydrochloric acid,
deionized water.

EXAMPLE 1

Synthesis of "ApiBisPhos EG"

(Mixture of 4'-(12,12-bisphosphono-3,6,9-trioxadodecanoxy)-7,5-dihydroxyflavone and 7-(12,12-bisphosphono-3,6,9-trioxadodecanoxy)-4',5-dihydroxyflavone)

Tetraethylenglycol Dibromide (1)

17.7 g (204 mmol) of lithium bromide were suspended in 80 ml of acetone under nitrogen. The suspension was cooled to 0-5° C. in an ice bath and 17.6 g (35 mmol) of tetraethylene glycol di(p-toluenesulfonate), dissolved in 30 ml of acetone, were added dropwise. After stirring at 0° C. for 30 min, the solution was stirred at RT for 48 hours. The white precipitate was then filtered off and washed with acetone. The acetone solution was concentrated. The residue was then taken up in 45 ml of toluene and shaken three times with water. The toluene phase was then concentrated using a rotary evaporator and dried under high vacuum. 9.5 g of a brown, clear liquid were obtained (yield: 85%).

$^1$H-NMR (MeOD, 300 MHz, ppm): δ=3.51-3.62(m, 12H, $CH_2$), 3.74(t, 4H, $CH_2CH_2Br$).

Tetraisopropyl 12-bromo-4,7,10-trioxadodecan-1,1-diylbisphosphonate (3)

0.35 g of sodium hydride (60% in mineral oil, 9 mmol) were washed 3 times with n-heptane under nitrogen and then suspended in 5 ml of dry tetrahydrofuran (THF). The suspension was cooled to 0-5° C. in an ice bath and 2.5 g (7 mmol) of tetraisopropyl methylenebisphosphonate were added dropwise. 9.5 g (30 mmol) of the compound (1) were dissolved in 10 ml of dry THF and added to the reaction mixture. The solution was stirred at RT for 96 hours and then 20 ml of aqueous sodium hydrogen carbonate solution (0.1 mol/l) were added. The THF was then rotary evaporated and the aqueous phase was shaken twice with toluene. The combined organic phases were concentrated using a rotary evaporator. The crude product was purified by column chromatography ($SiO_2$; ethyl acetate/n-heptane, 80:20, v/v) and dried under high vacuum. 1.9 g of a yellowish oil were obtained (yield: 45%).

$^1$H-NMR (DMSO-d6, 300 MHz, ppm): δ=1.23-1.29(m, 24H, $CH_3$), 1.85-2.05(m, 2H, $CH_2CH$), 2.36(tt, 1H, CH), 3.41-3.61(m, 12H, $CH_2O+CH_2Br$), 3.74(t, 2H, $CH_2CH_2Br$), 4.53-4.72(m, 4H, $CH(CH_3)_2$).

Mixture of 4'-(12,12-tetraisopropylbisphosphonato-3,6,9-trioxadodecanoxy)-7,5-dihydroxyflavone and 7-(12,12-tetraisopropylbisphosphonato-3,6,9-trioxadodecanoxy)-4',5-dihydroxyflavone (5)

0.5 g (1.8 mmol) of apigenin and 53 mg (0.9 mmol) of KOH were initially charged in 10 ml of DMSO. To this suspension was added 0.5 g (0.9 mmol) of tetraisopropyl 12-bromo-4,7,10-trioxadododecan-1,1-diyl bisphosphonate (3) and the mixture then stirred at 120° C. for 2 hours. After cooling to RT, the solution was precipitated with 40 ml of water and the precipitate was separated off by centrifugation. The precipitate was air dried for 72 hours. The crude product was then purified by column chromatography (1st chromatography n-heptane/ethanol, 60:40, v/v; 2nd chromatography $SiO_2$, 1st eluent n-heptane/ethanol, 70:30, v/v, 2nd eluent, ethanol; 3rd chromatography $SiO_2$, n-heptane/ethanol, 70:30, v/v), concentrated in a rotary evaporator and then dried under high vacuum. 0.15 g of a yellowish gel were obtained (yield: 22%).

$^1$H-NMR (DMSO-d6, 300 MHz, ppm): δ=1.21-1.35(d, 24H, $CH_3$), 1.85-2.05(m, 2H, $CH_2CH$), 2.35(tt, 1H, CH), 3.41-3.63(m, 10H, $CH_2O$) , 3.63-3.81 (m, 2H, $CH_2CH_2OC_{4'}/CH_2CH_2OC_7$) , 4.18-4.26 (m, 2H, $CH_2OC_{4'}/CH_2OC_7$), 4.53-4.70 (m, 4H, $CH(CH_3)_2$), 6.19/6.38 (s, 2H, H-$C_6$), 6.49/6.78 (s, 2H, H-$C_6$), 6.83 (s, 2H, H-$C_3$), 6.93/7.12(d, 2H, H-$C_{3'}$, H-$C_{5'}$), 7.95/8.02 (d, 2H, H-$C_{2'}$, H-$C_{6'}$), 12.93 (s, 1H, HO-$C_5$).

Mixture of 4'-(12,12-bisphosphono-3,6,9-trioxadodecanoxy)-7,5-dihydroxyflavone and 7-(12,12-bisphosphono-3,6,9-trioxadodecanoxy)-4',5-dihydroxyflavone (ApiBisPhosEG) (7)

4 ml of 0.5N hydrochloric acid solution were added to 0.14 g of mixture (5). This mixture was then stirred in a microwave (microwave: Discover CEM, power: 150W) at 150° C. for 1 hour. The dilute hydrochloric acid was then rotary evaporated and the product was dried under high vacuum. 0.11 g of a yellow-brown gel were obtained (yield: 100%).

$^1$H-NMR (DMSO-d6, 300 MHz, ppm): δ=1.87-2.20(m, 2H, $CH_2CH+CH$), 3.44-3.63(m, 10H, $CH_2O+CH_2CH_2OC_{4'}/CH_2CH_2OC_7$), 3.75-3.82(m, 2H, $CH_2CH_2OC_{4'}/CH_2CH_2OC_7$), 4.18-4.26 (m, 2H, $CH_2OC_{4'}/CH_2OC_7$), 6.21/6.38(s, 2H, H-$C_6$), 6.49/6.78(s, 2H, H-$C_8$), 6.83(s, 2H, H-$C_3$), 6.95/7.12(d, 2H, H-$C_{3'}$, H-$C_{5'}$), 7.95/8.02(d, 2H, H-$C_{2'}$, H-$C_{6'}$).

EXAMPLE 2

Synthesis of "ApiBisPhos UD"

(Mixture of 4'-(11,11-bisphosphonoundecanoxy)-7,5-dihydroxyflavone and 7-(11,11-bisphosphonoundecanoxy)-4', 5-dihydroxyflavone)

Tetraisopropyl 11-bromoundecan-1,1-diylbisphosphonate (2)

1.4 g of sodium hydride (60% in mineral oil, 35 mmol) were washed 3 times with n-heptane under nitrogen and then suspended in 15 ml of dry tetrahydrofuran (THF). The suspension was cooled to 0-5° C. in an ice bath and 10.0 g (29 mmol) of tetraisopropyl methylenebisphosphonate were added dropwise. 39.2 g (130 mmol) of 1,10-dibromodecane were dissolved in 25 ml of dry THF and added to the reaction mixture. The solution was stirred at RT for 48 hours and then 30 ml of aqueous sodium hydrogen carbonate solution (0.1 mol/l) were added. The THF was then rotary evaporated and the aqueous phase was shaken twice with toluene. The combined organic phases were concentrated using a rotary evaporator. Using column filtration ($SiO_2$, 1st eluent: heptane/ethyl acetate 1:1, v/v; 2nd eluent: ethanol), the excess dibromodecane was then removed. The crude product was purified by column chromatography ($SiO_2$; ethyl acetate/ethanol, 90:10, v/v). 6.4 g of a yellowish oil were obtained (yield: 39%).

$^1$H-NMR (DMSO-d6, 300 MHz, ppm): δ=1.12-1.42(m, 36H, $CH_2+CH_3$), 1.43-1.59(m, 2H, $CH_2$), 1.60-1.89(m, 4H, $CH_2CH_2Br+CH_2CH$), 2.16 (tt, 1H, CH), 3.51(t, 2H, $CH_2Br$), 4.53-4.75(m, 4H, CH $(CH_3)_2$).

Mixture of 4'-(11,11-tetraisopropylbisphosphonatoundecanoxy)-7,5-dihydroxyflavone and 7-(11,11-tetraisopropylbisphosphonatoundecanoxy)-4',5-dihydroxyflavone (4)

0.5 g (1.8 mmol) of apigenin and 52 mg (0.9 mmol) of potassium hydroxide (KOH) were initially charged in 10 ml of dimethyl sulfoxide (DMSO). To this suspension was added 0.5 g (0.9 mmol) of tetraisopropyl 11-bromoundecan-1,1-diylbisphosphonate (2) and the mixture then stirred at 120° C. for 2 hours. After cooling to RT, the solution was precipitated by adding 40 ml of water and the precipitate was separated off by centrifugation. The precipitate was dried under high vacuum. The crude product was then purified by column chromatography (1st chromatography $SiO_2$; gradient elution ethyl acetate/ethanol; 2nd chromatography $SiO_2$, ethyl acetate/ethanol, 95:5, v/v; 3rd chromatography $SiO_2$, n-heptane/ethanol, 90:10, v/v), concentrated in a rotary evaporator and then dried under high vacuum. 0.16 g of a yellowish gel were obtained (yield: 24%).

$^1$H-NMR (DMSO-d6, 300 MHz, ppm): δ=1.17-1.37(m, 34H, $CH_2+CH_3$), 1.37-1.58 (m, 4H, $CH_2$), 1.59-1.84 (m, 4H, $CH_2CH_2O+CH_2CH$), 2.16 (tt, 1H, CH), 4.08 (t, 2H, $CH_2O$), 4.53-4.72 (m, 4H, $CH(CH_3)_2$), 6.19/6.32(s, 2H, H-$C_6$), 6.49/6.73 (s, 2H, H-$C_8$), 6.78(s, 2H, H-$C_3$), 6.89/7.06(d, 2H, H-$C_{3'}$, H-$C_{5'}$), 7.92/7.94 (d, 2H, H-$C_{2'}$, H-$C_{6'}$) .

Mixture of 4'-(11,11-bisphosphonoundecanoxy)-7,5-dihydroxyflavone and 7-(11,11-bisphosphonoundecanoxy)-4', 5-dihydroxyflavone) (ApiBisPhos UD) (6)

4 ml of 0.5N hydrochloric acid solution were added to 0.15 g of mixture (4). This mixture was then stirred in a microwave (microwave: Discover CEM, power: 150W) at 150° C. for 1 hour.

The dilute hydrochloric acid was then rotary evaporated and the product was dried under high vacuum. 0.12 g of a yellow-brown gel were obtained (yield: 100%).

$^1$H-NMR (DMSO-d6, 300 MHz, ppm): δ=1.14-1.38(m, 10H, $CH_2$), 1.37-1.58 (m, 4H, $CH_2$), 1.62-1.84 (m, 4H, $CH_2CH_2O+CH_2CH$), 1.86-2.08 (m, 1H, CH) 4.08 (t, 2H, $CH_2O$), 6.21/6.34 (s, 2H, H-$C_6$), 6.51/6.75 (s, 2H, H-$C_8$), 6.82 (s, 2H, H-$C_3$), 6.94/7.09(d, 2H, H-$C_{3'}$, H-$C_{5'}$), 7.95/8.00 (d, 2H, H-$C_{2'}$, H-$C_{6'}$).

The proportion of the compound 7-(11,11-bisphosphonoundecanoxy)-4', 5-dihydroxyflavone in the isomeric mixture (6) was significantly greater than the proportion of the compound 4'-(11,11-bisphosphonoundecanoxy)-7,5-dihydroxyflavone. The synthetic route is designed in such a way that this compound is present in the isomeric mixture (6) in a clear excess (>70%).

Using the SeeSAR simulation software (BioSolveIT GmbH), the binding affinity of the compounds was simulated using the example of glucosyltransferase C (3AIE, 2.1A) from *S. mutans*. This showed an increased binding affinity of 7-(11,11-bisphosphonoundecanoxy)-4', 5-dihydroxyflavone compared to 4'-(11,11-bisphosphonoundecanoxy)-7,5-dihydroxyflavone.

EXAMPLE 3

Inhibitory Effect of Apigenin (Prior Art) and the Inventive Flavonoid Derivative "ApiBisPhos UD" on the Glucosyltransferase Activity of *S. mutans*

It was investigated whether the "ApiBisPhos UD" synthesized according to Example 2 had an influence on the activity of the glucosyltransferases of *S. mutans* as is to be expected from the apigenin known from the prior art. For this purpose, the test substance was resuspended in a DMSO/ethanol mixture (20/80%) and then diluted in the reaction mixture to the concentration to be tested (final concentration DMSO/ethanol 2/8%). The glucosyltransferase GtfC (0.3 µg, nzytech) was incubated in 100 mM potassium phosphate buffer, pH 6.0 with 30 mM sucrose for one hour at 37° C. in the presence of the test substances. As a positive control, the enzyme activity was measured in the presence of DMSO/ethanol (2/8%). To demonstrate Gtf enzyme activity, the fructose eliminated during glucan synthesis was detected via a multi-stage enzyme reaction. For this purpose, the D-fructose and D-glucose assay kit from Megazyme (K-FRUGL) was used.

Principle of Detection:

D-glucose and D-fructose are phosphorylated in the presence of adenosine-5-triphosphate (ATP) to glucose-6-phosphate (G-6-P) and fructose-6-phosphate (F-6-P) by the enzyme hexokinase (HK), producing adenosine 5'-diphosphate (ADP) (1), (2).

$$\text{D-Glucose} + \text{ATP} \xrightarrow{\text{(HK)}} \text{G-6-P} + \text{ADP} \quad (1)$$

$$\text{D-Fructose} + \text{ATP} \xrightarrow{\text{(HK)}} \text{F-6-P} + \text{ADP} \quad (2)$$

In the presence of the enzyme glucose-6-phosphate dehydrogenase (G6P-DH), G-6-P is oxidized to gluconate-6-phosphate by nicotinamide adenine dinucleotide ($NADP^+$). This produces reduced nicotinamide adenine dinucleotide phosphate (NADPH) (3).

$$\text{G-6-P} + \text{NADP}^+ \xrightarrow{\text{(G6P-DH)}} \text{gluconate-6-phosphate} + \text{NADPH} + \text{H}^+ \quad (3)$$

The amount of NADPH formed in this reaction corresponds stoichiometrically to the amount of D-glucose. The absorption of NADPH is measured at 340 nm.

After completion of the reaction (3), F-6-P is converted to G-6-P by phosphoglucose isomerase (PGI) (4).

$$\text{F-6-P} \underset{}{\overset{\text{(PGI)}}{\rightleftharpoons}} \text{G-6-P} \quad (4)$$

The G-6-P formed reacts in turn with $NADP^+$ to form gluconate-6-phosphate and NADPH, which leads to a further increase in absorption and correlates stoichiometrically with the amount of D-fructose.

Figure 1:
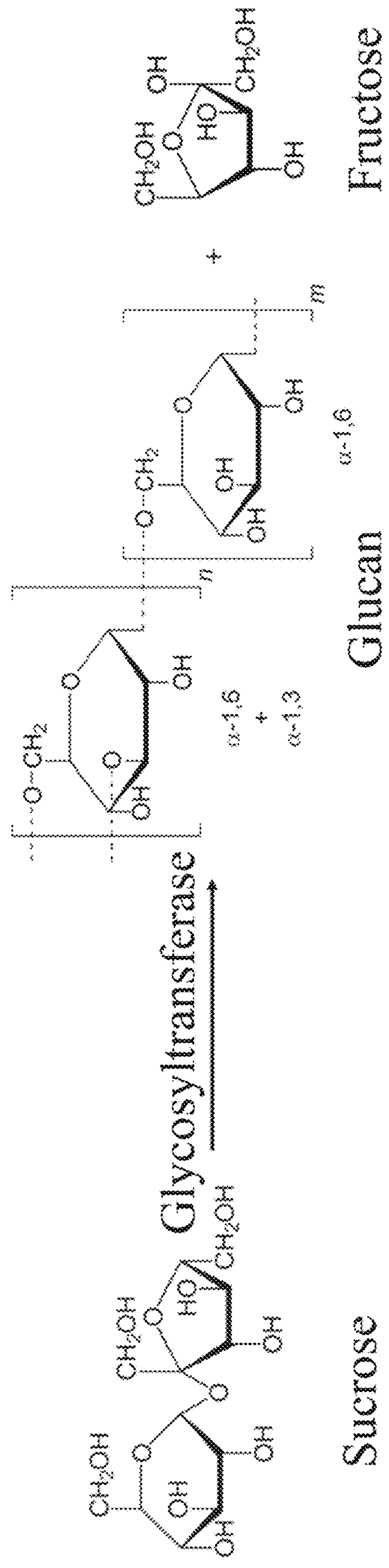
FIG. 1 is an illustration of glucan synthesis by glucosyltransferases.
Figure 2:
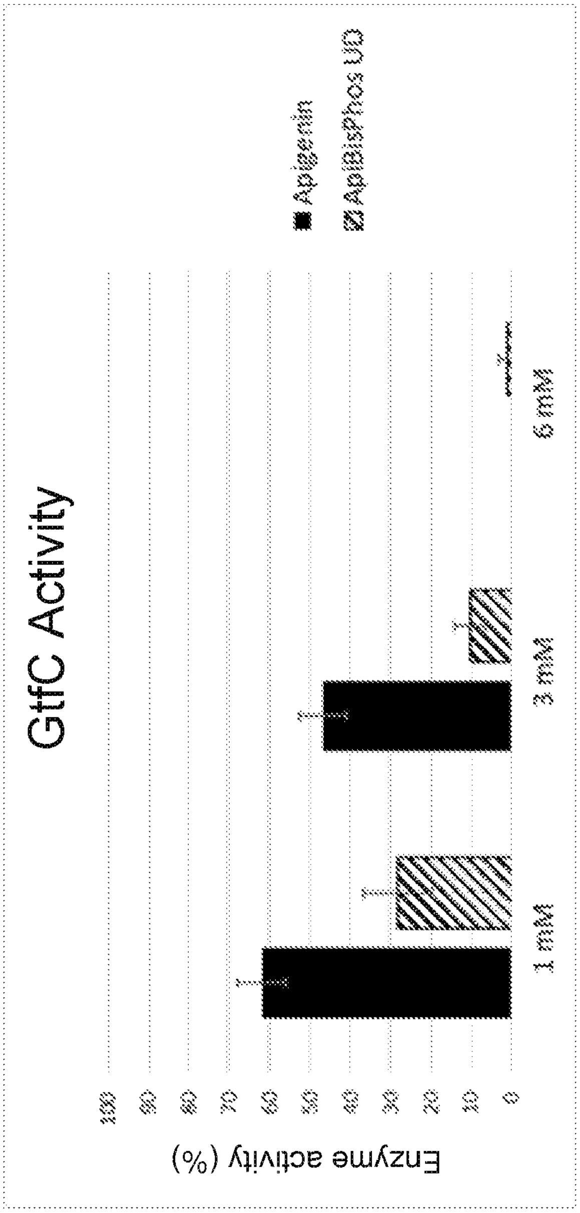
FIG. 2 shows the activity of glucosyltransferase C of *S. mutans*.

The results are shown in FIG. 2. FIG. 2 shows the activity of glucosyltransferase C of *S. mutans*. 9 independent reaction batches were measured in triplicate and the enzyme activity was normalized to the solvent control. Apigenin 6 mM could not be tested due to insufficient solubility.

As can be seen from FIG. 2, the activity of glucosyltransferase C of *S. mutans* was surprisingly significantly more strongly inhibited by the flavonoid derivative ApiBisPhos UD according to the invention compared to the flavonoid apigenin. The remaining enzyme activity when using ApiBisPhos UD is less than 30% at 1 mM and about 10% at 3 mM (hatched bars), several times less than the enzyme activity when using apigenin (black bars). Expressed another way: The activity of glucosyltransferase C is inhibited in the presence of 1 mM ApiBisPhosUD by 72±9%, at 3 mM by 90±4% and at 6 mM by 99±2%. In comparison, the enzyme activity was inhibited by only 38±10% at 1 mM apigenin and by only 53±6% at 3 mM apigenin.

EXAMPLE 4

Adhesion of the Inventive Flavonoid Derivative "ApiBisPhos UD" to Hydroxyapatite Investigated in addition was the adhesion of the inventive flavonoid derivative "ApiBisPhos UD" to hydroxyapatite, a substance that largely determines the tooth surface and is suitable as an adhesive contact. For this purpose, 5 mg of hydroxyapatite (HAP) were moistened with saliva for 30 minutes and then incubated with ApiBisPhos UD (5, 10, 50, 100 mM in DMSO/ethanol mixture; 20/80%) for 30 minutes. The amount of unbound ApiBisPhos UD in the supernatant was then determined by thin-layer chromatography. The results of this experiment are presented in FIG. 3 and show that the flavonoid derivative "ApiBisPhos UD" according to the invention adheres excellently to the hydroxyapatite moistened with saliva with more than 96% of the applied ApiBisPhos UD substance binding.

EXAMPLE 5

Effect of "ApiBisPhos UD" and "ApiBisPhos EG" Bound to Hydroxyapatite on *S. mutans* Gtf70C ApiBisPhos UD was bound to HAP as described in Example 4 and then incubated with GtfC as described in Example 3. The HAP was then centrifuged off and the GtfC activity in the supernatant was then determined as described in Example 3. A similar procedure was followed with the further flavonoid derivative "ApiBisPhos EG" according to the invention. The results are presented in FIG. 4 and show that both ApiBisPhos UD and ApiBisPhos EG bound to hydroxyapatite inhibit the GtfC enzyme activity of *S. mutans* to a considerable degree. In other words, the further example of a flavonoid derivative according to the invention ("ApiBisPhos EG") confirms the successful functioning of the present invention as the basis for achieving the advantage according to the invention based on the adhesion of the flavonoid derivative according to the invention to the tooth surface comprising hydroxyapatite, so that the flavonoid derivative can prevent or to a great extent inhibit the formation of biofilm causing dental diseases on the tooth surfaces treated with the flavonoid derivative in the long term.

EXAMPLE 6

Effect of "ApiBisPhos UD" Bonded to Hydroxyapatite (HAP) on the Formation of *S. mutans* Biofilm In this example, it was investigated whether "ApibisPhos UD" has a significant influence on *S. mutans*-mediated biofilm formation using hydroxyapatite discs coated with saliva under conditions simulating the oral cavity.

For this purpose, sterile hydroxyapatite disks (Clarkson Chromatography Products Inc., Ø5 mm×2 mm) were coated with saliva (Lee Biosolutions, human pooled donors) as substrate for 60 minutes and then incubated with ApiBisPhos UD (60 μl; 10 mM in DMSO/ethanol mixture, 20/80%) for 60 minutes. After washing twice with DPBS, these pretreated hydroxyapatite disks were coated with *S. mutans* preculture ($1.5\times10^8$ bacteria per ml in Balmelli broth) and cultured aerobically at 37° C. for 24 hours. The grown biofilm was fixed with 100% ethanol (30 min, 25° C.), stained with 0.06% (w/v) crystal violet (60 min, 25° C.) and the dye eluted with 30% (v/v) acetic acid quantified by measuring the absorbance at 570 nm. The measured values were set in relation to the solvent control (DMSO/ethanol mixture; 20/80%), i.e. without the use of ApibisPhos UD.

The results of 5 independent experiments carried out in triplicate show that the flavonoid derivative "ApiBisPhos UD" according to the invention inhibits the formation of biofilms on HAP surfaces by 26±9% under the test conditions described.

In other words, the further example of the flavonoid derivative according to the invention ("ApiBisPhos UD") also confirms the successful functioning of the present invention.

This example also demonstrates the statistically significant flavonoid derivative-mediated inhibition of *S. mutans*-induced biolfilm formation on a hydroxyapatite disk simulating the tooth surface with the flavonoid derivative ApiBisPhos UD bonded thereto.

The invention claimed is:

1. A method for the prophylaxis and/or treatment of oral disease, comprising bonding a dental preparation to a tooth surface, wherein the dental preparation comprises at least one flavonoid derivative, wherein the at least one flavonoid derivative is a compound of formula (I):

(Formula I)

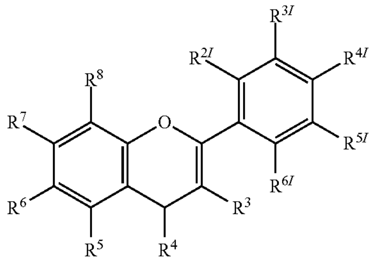

where i) $R^4$=H, OH or an oxo group (═O);

ii) $R^3$, $R^5$, $R^6$, $R^7$, $R^8$, $R^{21}$, $R^{3I}$, $R^{4I}$, $R^{6I}$, $R^{6I}$ are each independently H, OH, $OR^1$ where $R^1$=methyl or acyl, rhamnose, glucose, oligoglucose, rutinose or Et-Q-Z where Et =O, i.e. O-Q-Z;

iii) at least one of the radicals $R^3$, $R^5$, $R^6$, $R^7$, $R^8$, $R^{2I}$, $R^{3I}$, $R^{4I}$, $R^{5I}$, $R^{6I}$ is Et-Q-Z where Et=O, i.e. O-Q-Z;

iv) Q is a spacer group, wherein the spacer group Q is an alkylene group, which may optionally be interrupted by an oxygen atom, a nitrogen atom and/or a polyoxyalkylene group; and v) Z is an adhesion group, said Z group being selected from the group consisting of:

$—COOR^2$, $—SO_2OR^2$, $—OPO(OR^2)_2$, $—PO(OR^2)_2$, $—CR^1 (PO(OR^2)_2)_2$, with $R^1$=H, OH or alkyl, $R^2$=H, alkyl or M, where M is a monovalent cation.

2. The method of claim 1, wherein the adhesion group Z is covalently bonded to the spacer group Q via a C—C bond, a C—S bond, a C—P bond, a C—O—P bond or a C—C—P bond.

3. The method of claim 1, wherein the adhesion group Z is $COOR^2$ and is coupled to the spacer group Q and said spacer Q comprises a linear alkylene group having 8 to 12 carbon atoms.

4. The method of claim 1, wherein the dental preparation comprises at least one further active ingredient selected from the group of flavonoids.

5. The method of claim 1, wherein the dental preparation further comprises a fluoridating agent selected from the group of metal fluorides, amine fluorides and fluoride complexes.

6. A method for the prophylaxis and/or treatment of oral disease, comprising bonding a dental preparation to a tooth surface, wherein the dental preparation comprises at least one flavonoid derivative, wherein the at least one flavonoid derivative is a compound of formula (II):

(Formula II)

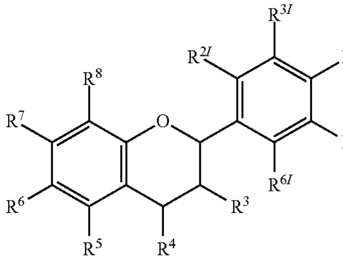

where i) $R^4$=H, OH or an oxo group (=O);

ii) $R^3$, $R^5$, $R^6$, $R^7$, $R^8$, $R^{2I}$, $R^{3I}$, $R^{4I}$, $R^{5I}$, $R^{6I}$ are each independently H, OH, $OR^1$ where $R^1$=methyl or acyl, rhamnose, glucose, oligoglucose, rutinose or Et-Q-Z where Et =O, i.e. O-Q-Z;

iii) at least one of the radicals $R^3$, $R^5$, $R^6$, $R^7$, $R^8$, $R^{2I}$, $R^{3I}$, $R^{4I}$, $R^{5I}$, $R^{6I}$ is Et-Q-Z where Et=O, i.e. O-Q-Z;

iv) Q is a spacer group, wherein the spacer group Q is an alkylene group, which may optionally be interrupted by an oxygen atom, a nitrogen atom and/or a polyoxyalkylene group; and v) Z is an adhesion group, said Z group being selected from the group consisting of:

$—COOR^2$, $—SO_2OR^2$, $OPO(OR^2)_2$, $—PO(OR^2)_2$, $—CR^1\ (PO(OR^2)_2)_2$, with $R^1$=H, OH or alkyl, $R^2$=H, alkyl or M, where M is a monovalent cation.

7. The method of claim 6, wherein the adhesion group Z is covalently bonded to the spacer group Q via a C—C bond, a C—S bond, a C—P bond, a C—O—P bond or a C—C—P bond.

8. The method of claim 6, wherein the adhesion group Z is $COOR^2$ and is coupled to the spacer group Q and said spacer Q comprises a linear alkylene group having 8 to 12 carbon atoms.

9. The method of claim 6, wherein the dental preparation comprises at least one further active ingredient selected from the group of flavonoids.

10. The method of claim 6, wherein the dental preparation further comprises a fluoridating agent selected from the group of metal fluorides, amine fluorides and fluoride complexes.

11. A method for the prophylaxis and/or treatment of oral disease, comprising bonding a dental preparation to a tooth surface, wherein the dental preparation comprises at least one flavonoid derivative, wherein the at least one flavonoid derivative is a compound of formula (III):

(Formula III)

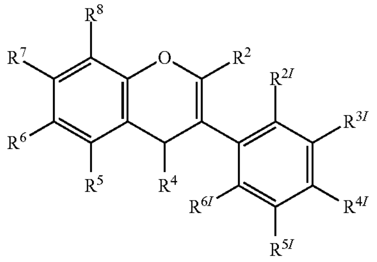

where i) $R^4$=H, OH or an oxo group (=O);

ii) $R^2$, $R^5$, $R^6$, $R^7$, $R^8$, $R^{2I}$, $R^{3I}$, $R^{4I}$, $R^{5I}$, $R^{6I}$ are each independently H, OH, $OR^1$ where $R^1$=methyl or acyl, rhamnose, glucose, oligoglucose, rutinose or Et-Q-Z where Et =O, i.e. O-Q-Z;

iii) at least one of the radicals $R^2$, $R^5$, $R^6$, $R^7$, $R^8$, $R^{2I}$, $R^{3I}$, $R^{4I}$, $R^{5I}$, $R^{6I}$ is Et-Q-Z where Et=O, i.e. O-Q-Z;

iv) Q is a spacer group, wherein the spacer group Q is an alkylene group, which may optionally be interrupted by an oxygen atom, a nitrogen atom and/or a polyoxyalkylene group; and v) Z is an adhesion group, said Z group being selected from the group consisting of:

$—COOR^2$, $—SO_2OR^2$, $—OPO(OR^2)_2$, $—PO(OR^2)_2$, $—CR^1\ (PO(OR^2)_2)_2$, with $R^1$=H, OH or alkyl, $R^2$=H, alkyl or M, where M is a monovalent cation.

12. The method of claim 11, wherein the adhesion group Z is covalently bonded to the spacer group Q via a C—C bond, a C—S bond, a C—P bond, a C—O—P bond or a C—C—P bond.

13. The method of claim 11, wherein the adhesion group Z is $COOR^2$ and is coupled to the spacer group Q and said spacer Q comprises a linear alkylene group having 8 to 12 carbon atoms.

14. The method of claim 11, wherein the dental preparation comprises at least one further active ingredient selected from the group of flavonoids.

15. The method of claim 11, wherein the dental preparation further comprises a fluoridating agent selected from the group of metal fluorides, amine fluorides and fluoride complexes.

* * * * *